United States Patent [19]
Ahn et al.

[11] Patent Number: 6,166,102
[45] Date of Patent: Dec. 26, 2000

[54] DENTURE ADHESIVE

[75] Inventors: Hyung-Kook Ahn, Dayton; Robert C. Gasman, Montville; Eddie Wong, New Providence, all of N.J.

[73] Assignee: Block Drug Company, Inc., Jersey City, N.J.

[21] Appl. No.: 09/207,309

[22] Filed: Dec. 8, 1998

[51] Int. Cl.[7] .......................... A61K 6/083; C09J 135/08; C08F 222/06; A61C 13/23

[52] U.S. Cl. .......................... 523/120; 524/238; 524/549; 524/559; 525/327.6; 525/329.6; 433/180

[58] Field of Search .............................. 523/120; 524/238, 524/549, 559; 525/327.6, 329.6; 433/180

[56] References Cited

U.S. PATENT DOCUMENTS

| | | | |
|---|---|---|---|
| 2,313,565 | 3/1943 | McDowell et al. | 260/78 |
| 3,121,043 | 2/1964 | Tobin et al. | 167/82 |
| 3,684,776 | 8/1972 | Field et al. | 260/78.5 |
| 3,729,452 | 4/1973 | Andress et al. | 260/78 |
| 3,878,151 | 4/1975 | Dachs et al. | 260/29.6 |
| 3,974,128 | 8/1976 | Block et al. | 526/14 |
| 4,182,800 | 1/1980 | Ringsdorf et al. | 525/375 |
| 4,874,604 | 10/1989 | Sramek . | |
| 5,066,709 | 11/1991 | Chaudhuri et al. | 524/516 |
| 5,115,033 | 5/1992 | Wong | 525/285 |
| 5,178,143 | 1/1993 | Kwak et al. | 128/639 |
| 5,294,681 | 3/1994 | Krupey | 525/327.6 |
| 5,298,568 | 3/1994 | Suzuki | 525/327.6 |
| 5,330,746 | 7/1994 | Friedman . | |
| 5,438,076 | 8/1995 | Friedman et al. | 424/49 |
| 5,521,256 | 5/1996 | Kwak et al. | 525/378 |
| 5,534,597 | 7/1996 | Krupey | 525/327.6 |
| 5,578,661 | 11/1996 | Fox et al. | 524/27 |
| 5,753,215 | 5/1998 | Mougin et al. | 424/70.11 |
| 5,760,166 | 6/1998 | Charles et al. | 525/327.8 |

FOREIGN PATENT DOCUMENTS

| | | |
|---|---|---|
| WO 97 10772 | 3/1997 | WIPO . |
| WO 98 43595A | 10/1998 | WIPO . |

*Primary Examiner*—Peter A. Szekely

[57] ABSTRACT

A denture adhesive comprising a copolymer salt at least partially cross-linked by lysine, histidine, arginine, nontoxic derivatives or family members of lysine, histidine or arginine and mixtures thereof.

15 Claims, No Drawings

DENTURE ADHESIVE

BACKGROUND OF THE INVENTION

1. Field of the Invention

The invention relates to denture adhesives and to processes for making and using denture adhesives.

2. Description of Related Art

Dentures are substitutes for missing teeth and serve as a replacement for all or some of the teeth found in the oral cavity. Despite diligent efforts by dental professionals and designers of dental prostheses, dentures do not always fit perfectly. Over time, even well-fitting dentures can become ill-fitting due to natural shrinkage and changes in the gum or mucous tissues. Therefore, adherent creams, liquids or powders are often used to secure or temporarily fix dentures within the mouth.

There are a number of desirable attributes of such a denture adhesive composition. The denture adhesive should develop a high degree of tack upon contact with saliva so that the dentures can be held in place as soon as they are seated in the mouth. It is also highly desirable that the saliva hydrated adhesive be spread over the denture-mucosa interface in order to seal the denture in place effectively. The mucilage should possess sufficient cohesive strength to withstand the stresses of mastication, which act to rupture the seal and thus dislodge the denture. The denture adhesive must also exhibit sufficient resistance to degradation under the extreme environmental changes that can occur in the oral cavity during such common actions as drinking hot or cold beverages. Of course, the adhesive must also be releasable so that the denture wearer may remove the dentures for cleaning and maintenance. Denture adhesives are generally sold as a cream, liner or strip, liquid or powder, and many examples are well known in the art.

A major factor in selecting one denture adhesive over another in the marketplace, however, remains the holding performance of a denture adhesive. Thus, workers in the field have been constantly seeking better holding performance.

Early denture adhesives contained finely ground particles of natural gums that expanded when wet to become a viscous gel, which acted as a cushion and an adherent between a denture plate and gum tissue. These denture adhesives, however, have been largely supplanted by polymeric denture adhesives in recent years.

A popular current choice for a polymeric denture adhesive comprises a methyl vinyl ether/maleic anhydride copolymer known as "Gantrez®." This polymer is combined with a number of other ingredients to form the final denture adhesive.

Polymers, of course, have been known for many years and have been used for many different purposes. Depending on the monomer or monomers selected, a polymer may have a vast array of properties and be useful for a number of different purposes. Once the basic constituents of the polymer or copolymer have been selected, any number of modifications may be made to affect various properties of the final polymer or copolymer. The chain length of the polymer may be regulated to be short or long, and, in the case of copolymers of two or more chemically distinct monomers, the order of the monomers may be regulated to form a block copolymer or an alternating copolymer or anything in between.

Once the structure of the polymer or copolymer has been defined, the properties of the polymer or copolymer may still be modified significantly by various chemical or physical methods. One method of modifying the properties of a polymer or copolymer is to modify various ligands that may be present on the polymer chain. For example, with a MVE/MA copolymer, the anhydride group may be hydrolyzed to the corresponding dicarboxylic acid. The carboxylic acid, in turn, may be fully or partially neutralized to form a salt or the carboxylic acid may be fully or partially esterified with various groups. The modification of the carboxylic acid leads to a change in the properties of the copolymer. The copolymer may be plasticized or otherwise modified by the addition of a cation or covalently bound ligand.

These ionic or covalent bonds may lead to crosslinking of the copolymer chains. If a salt is formed with a divalent cation, the cation may form an ionic "cross-link" between two copolymer chains. Such a "cross-link" may be very easily dissociated in the presence of water. If a compound contains two or more groups capable of forming an ester with a carboxylic acid ligand, then covalent cross-links may be formed between adjacent copolymer chains. These covalent cross-links may have more or less resistance to hydrolysis depending on the ligand chosen.

Polymers and copolymers of anhydrides, including maleic anhydride, have been known for a long time and have been used for many purposes. For example, U.S. Pat. No. 2,313,565 to McDowell et al., issued Mar. 9, 1943, is directed to a copolymer of an acid anhydride with a vinyl ether monomer. The anhydride may be treated with ammonia or a primary or secondary amine to form an imide. The copolymer is useful as a sheeting or film base.

Anhydride copolymers have also been used as carriers for sustained release pharmaceuticals, at least where the pharmaceutical could be used as an amine salt. In U.S. Pat. No. 3,121,043 to Tobin et al., issued Feb. 11, 1964 the anhydride is lightly cross-linked with the pharmaceutical salt, and the active pharmaceutical is released over time as the amine link is hydrolyzed. A copolymer of maleic anhydride and methotrexate for treating tumors is discussed in U.S. Pat. No. 4,182,800 to Ringsdorf et al., issued Jan. 8, 1980.

Anhydride copolymers may also be used in hair spray or cosmetics (U.S. Pat. No. 3,974,128 to Block et al., issued Aug. 10, 197G and U.S. Pat. No. 5,753,215 to Mougin et al., issued May 19, 1998); as thickening agents (U.S. Pat. No. 3,684,776 to Field et al., issued Aug. 15, 1972 and U.S. Pat. No. 3,878,151 to Dachs et al., issued Apr. 15, 1975); and as anti-static agents for flammable liquids (U.S. Pat. No. 3,729,452 to Andress et al., issued Apr. 24, 1973). Mougin discusses MVE/MA copolymers monoesterified with butanol and neutralized by diamines or polyvalent metal salts. The diamines include lysine, arginine and cystine, and the polyvalent metal salts include bromides, chlorides, nitrates, acetates, carbonates and sulphates of calcium, zinc, magnesium, barium, aluminum and zirconium.

Anhydride copolymers have been used to support biological molecules in U.S. Pat. No. 5,760,166 to Charles et al., issued Jun. 2, 1998. The copolymer has a nitrogen or sulfur ligands such as ethanolamine or mercaptoethanol on some of the carboxyl groups. Anhydride copolymers have also been used to precipitate proteins from aqueous media in U.S. Pat. No. 5,534,597 to Krupey, issued Jul. 9, 1996 and U.S. Pat. No. 5,294,681 to Krupey, issued Mar. 15, 1994. The copolymer is a water insoluble cross-linked polyhydroxy polycarboxylic acid having at least two strands linked by at least one diamine cross-linking agent.

A gel-forming system useful in wound dressings contains a mixture of polymers as discussed in U.S. Pat. No. 5,578, 661 to Fox et al., issued Nov. 26, 1996. The system has a water-soluble polymer, such as polyethylene oxide, an acid containing polymer, such as a MVE/MA copolymer, and an amino-containing polymer, such as polysaccharides or poly-L-lysine. Another gel is discussed in U.S. Pat. No. 5,521,256 to Kwak et al., issued May 28, 1996. Sodium hydroxide is added to a crosslinked MVE/MA copolymer, thereby forming a gel solution.

Denture adhesives are not the only adhesive materials that contain anhydride copolymers. U.S. Pat. No. 5,298,568 to Suzuki, issued Mar. 29, 1994, is directed to an adhesive useful in recycling of corrugated paper. The adhesive is a copolymer of an alpha-olefin and maleic anhydride. The copolymer may be modified by the addition of hydroxyl, amino, aziridinyl and mercapto groups.

Another adhesive, used to help bond polymers such as ethylene or vinyl alcohol copolymers to polyolefins and polyamides, is discussed in U.S. Pat. No. 5,115,033 to Wong, issued May 19, 1992, the adhesive contains a polymer and a catalytic agent. The polymer is a polyolefin grafted onto an unsaturated carboxylic acid or anhydride. The catalytic agent is a monoalkyl phosphate or alkylamine.

An anhydride polymer is part of an electrically conductive gel composition for use in establishing a low resistance contact between an electrode and a biological body in U.S. Pat. No. 5,178,143 to Kwak et al., issued Jan. 12, 1993. While this gel is not, strictly speaking, an adhesive, it is made from a crosslinked, neutralized copolymer of maleic anhydride and vinyl ether.

One problem with denture adhesive copolymers, particularly MVE/MA copolymers, is that covalent cross-linking is not an attractive approach to fine-tuning the desired properties of the denture adhesive. Covalent cross-linking can reduce the affinity of the copolymer for water, which can have an adverse effect on the properties of the copolymer for some important applications.

Cross-linking agents have been tried with denture adhesives, including propylene glycol and glycerin in U.S. Pat. No. 5,696,181 to Chang et al., issued Dec. 9, 1997.

Bioadhesives that may be useful as denture adhesive ingredients have also been made with anhydride copolymers. U.S. Pat. No. 5,066,709 to Chaudhuri et al., issued Nov. 19, 1991, is directed to a bioadhesive composition comprising a MVE/MA copolymer monofunctional lactam side groups.

One formulating a denture adhesive must consider organoleptic properties in addition to the functional aspects of a cross-linking agent. A certain amount of a cross-linking agent can be expected to hydrolyze in an aqueous environment such as the oral cavity, especially if the covalent cross-link is accomplished through an ester linkage. Thus, the cross-linking agent itself must be nontoxic at a minimum and should also not provide an unpleasant taste, texture or other sensation to the user.

SUMMARY OF THE INVENTION

The principal object of the present invention therefore is to provide a denture adhesive having an improved holding performance over currently marketed denture adhesives.

It is an advantage of the invention that the improved hold is achieved without adversely affecting the organoleptic qualities of a denture adhesive. It is a further advantage that the amide linkages between the cross-linking compound and the copolymer appear to hydrolyze relatively slowly, allowing for improved hold over a long period of time.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and following the purpose of the invention, as embodied and broadly described herein, the invention provides a denture adhesive comprising a denture adhesive effective amount of a cross-linked polymer or polymer salt, wherein the polymer or polymer salt comprises an alkyl vinyl ether and a polymerizable anhydride which is at least partially cross-linked by lysine, histidine, arginine, nontoxic derivatives or family members of lysine, histidine or arginine and mixtures thereof.

Cross-linking provides improved holding power for the denture adhesive of the invention by raising the molecular weight of the copolymer.

To further achieve the foregoing objects and by the purpose of the invention, the invention further provides a method of making a copolymer salt comprising the steps of cross-linking an alkyl vinyl ether/polymerizable anhydride copolymer with lysine, histidine, arginine, nontoxic derivatives or family members of lysine, histidine or arginine and mixtures thereof; at least partially hydrolyzing the anhydride to form the acid and neutralizing the acid to form a salt thereof.

DESCRIPTION OF THE PREFERRED EMBODIMENTS

Reference will now be made in detail to the presently preferred embodiments of the invention.

A denture adhesive in accordance with the invention begins with the polymer or copolymer to be used. Polymers or copolymers containing acid anhydride groups are capable of forming cross-links with lysine, histidine, arginine, nontoxic derivatives or family members of lysine, histidine or arginine and mixtures thereof and are within the scope of the invention to the extent that such polymers or copolymers are useful as ingredients in denture adhesives. A preferred embodiment of the invention uses a copolymer of an acid anhydride. A more preferred embodiment of the invention uses a copolymer of an alkyl vinyl ether with an unsaturated acid anhydride, and a highly preferred embodiment of the invention uses a methyl vinyl ether/maleic anhydride copolymer. Ethylene/maleic anhydride copolymers, vinyl pyrrolidone/maleicanhydride copolymers, isobutylene/maleic anhydride copolymers, vinyl acetate/maleic anhydride copolymers, alkylacrylate/maleicanhydride copolymers, vinyl ether/citraconic anhydride copolymers, and vinyl ether/itaconic anhydride copolymers and many other 1:1 alternating copolymers of an unsaturated acid anhydride and another vinylmonomor may also be used in the invention.

Of the many methyl vinyl ether/maleic acid or anhydride copolymers that may be used, copolymers manufactured under the name "Gantrez®" are preferred. Preferred Gantrez polymers include the Gantrez AN series of the anhydride form of the polymer, commercially available from International Specialty Products of Wayne, New Jersey.

Preferably, the polymer has a specific viscosity of at least about 1.0 and preferably from about 2.5 to about 6.0. Specific viscosity is measured as a solution of 1 g of copolymer in 100 ml of methyl-ethyl ketone (MEK) at 25 degrees centigrade. Higher and lower specific viscosities are within the scope of the invention, but lower than 2.5 specific viscosity polymers are not preferred because these polymers can have poor cohesive properties in denture adhesive formulations.

Partial salts of the copolymers must be used, including mixed partial salts of different cations. Preferred cations include, but are not limited to, calcium, magnesium, strontium, ferrous iron, sodium, potassium, zirconium, zinc, and other non-toxic cations. Preferably, the acid groups are not entirely cross-linked and neutralized.

A 1% solution of the copolymer in deionized water should have a pH of from about 4 to about 8, preferably from about 4.5 to about 7.5, and most preferably from about 5 to about 7.

The cross-linking agent of the invention includes the naturally occurring amino acids lysine, histidine, arginine, nontoxic derivatives or family members of lysine, histidine or arginine and mixtures thereof. The preferred amino acid, lysine (2,6 diaminohexanoic acid), is an amino acid having the structure: $NH_2CH_2CH_2CH_2CH_2CH(NH_2)COOH$. Nontoxic derivatives, including, but not limited to, acid salts thereof and substituted amines capable of forming cross-links with the acid anhydride groups on the MVE/MA copolymer may be within the scope of the invention as may nontoxic diamino acids with a shorter or longer chain length, side chains or ligands and derivatives thereof.

The amount of cross-linking in the copolymer needs to be controlled. Excess cross-linking can make a batch of copolymer unsuitable for use. Preferably, the percent substitution of lysine in the polymer is less than about 5% and more than about 0.005%. More preferably, the percent substitution is more than about 0.01% and less than about 1% and most preferably the percent substitution is about 0.05% to 0.5%.

To make the cross-linked copolymer in accordance with the invention, the copolymer and the cross-linking agent are dispersed in water at room temperature (about 10% solids content) and mixed to form the cross-linked polymer. The lysine is very reactive with the anhydride groups in the polymer, and the anhydride groups react with the amino groups in the lysine in preference to hydrolysis in water. Without being limited by theory, we speculate that the amino group immediately adjacement to the carboxyl group in lysine is reacting with the anhydride via a mechanism known as the Dakin-West reaction. In this reaction, an acid anhydride, $(R' CO)_2O$ reacts with an alpha amino acid, $R-CH(NH_2)-COOH$, to acylate the amine group and form a cross-link through the alpha amino group and the alpha carboxyl group, $R'-CO-CHR-NH-CO-R'$, and $CO_2$. This bond is a is a true covalent bond and is not vulnerable to hydrolysis when the denture adhesive is placed in an aqueous environment in the mouth. The other amino group may then react with an anhydride group in another polymer chain to form a cross-linked polymer system.

A partial salt is then formed by full or partial hydrolysis of the remaining anhydride groups and partial neutralization of the resulting acid. The solution or dispersion is then dried to form a film or a flake of the desired copolymer.

The dried copolymer partial salt is milled to a suitable particle size material and may then be combined with other ingredients to form a denture adhesive.

The copolymer salt is combined with a hydrophilic polymer to enhance the ability of the denture adhesive to form a swellable, tacky and viscous adhesive material upon contact with saliva in the oral cavity. The preferred hydrophilic polymers are selected from the group comprising sodium carboxymethyl cellulose, sodium alginate, polyoxyethylene oxide, karaya gum, hydroxyethyl cellulose, locust bean gum, xanthan gum, carrageenan, methyl cellulose and mixtures thereof. The hydrophilic polymer may comprise from about 10 to about 60% by weight of the final denture adhesive, preferably from about 15% to about 55% by weight and most preferably from about 20% to about 50% by weight.

The cross-linked polymer salt of the invention may be incorporated into the denture adhesive composition in an effective amount as the sole adhesive component or in combination with other water soluble polymers and excipients as is known in the art such as fillers, lubricants, flavors, coloring agents, preservatives and the like. Mineral oil, vegetable oil, petrolatum, preservatives, such as the alkyl parabens, fumed silica and mint flavor are examples of common excipients used in known commercial denture adhesive compositions. The amounts employed will be varied depending on the particular copolymer salt used and the cross-linking agent, the degree of cross-linking, the ratio of the inorganic cations to the organic cross-linker, the amount of the hydrophilic polymer and the other constituents of the adhesive compositions. In general, the crosslinked copolymer salt comprises from about 10% to about 70% by weight of the adhesive compositions, and preferably from about 20% to about 60%. The suitable hydrophilic polymers include both natural and synthetic gums, preferably sodium carboxymethyl cellulose, polyethylene oxide and sodium alginate.

To demonstrate that a copolymer of methyl vinyl ether and maleic anhydride could have its performance improved by increasing its molecular weight using an alpha amine carboxylic acid cross-linking agent, the following non-limiting examples were carried out.

Examples 1–9

A Lysine-poly methylvinyl ether/maleic acid was prepared by adding 99.62 g of a methylvinyl ether/maleic anhydride copolymer (GANTREZ AN 169) to 1250 ml. of vigorously mixed deionized water. 0.38 g of L-Lysine monohydrate was added to the mix, and the resulting mixture was held at room temperature for 30 minutes with continuous mixing.

The mixture was then heated to 85–90 degrees C and held at that temperature for 2 hours with continuous mixing. The resulting solution was discharged into trays (while maintaining batch temperature and mixing speed) and dried in an 85 degrees C oven. The resulting copolymer was a 0.36% substituted Lysine GANTREZ Acid.

The same method was used with different amounts of lysine to form the different DS Lysine-GANTREZ Acid copolymers shown in Table 1.A Comparative example of a copolymer that had not been cross-linked was also prepared.

The viscosity of the dry lysine-GANTREZ Acid was measured by milling the dry copolymer and then preparing a 0.25 weight percent solution of the copolymer in deionized water. The viscosity of the solution was then measured using a Cannon-Fenske Viscometer at 25 degrees C. These results are shown in Table 1.

TABLE 1

Viscosity Measurements

| Material Tested | Specific Viscosity ($\eta_{sp}$) |
| --- | --- |
| 0.00% Lysine | 4.06 |
| 0.03% Lysine | 4.21 |
| 0.06% Lysine | 3.63 |
| 0.09% Lysine | 4.12 |
| 0.12% Lysine | 3.96 |
| 0.24% Lysine | 4.15 |
| 0.30% Lysine | 4.36 |
| 0.36% Lysine | 5.09 |
| 0.48% Lysine | 6.66 |

We also observed the change in the molecular weight the addition of lysine. The increase in solution viscosity with increasing amounts of lysine shows that the molecular weight of the copolymer increases with the addition of lysine. After the addition of 0.24 percent substituted lysine, polymer molecular weight started to increase. Starting with the 0.6 percent substituted lysine GANTREZ acid (results not shown in Table 1), the molecular weight increased to a point where it was difficult to measure the viscosity.

Examples 10–17

A partial calcium salt of poly methylvinyl ether/maleic acid was prepared by adding 74.87 g GANTREZ AN 169 to 1250 ml. of vigorously mixed deionized water. Then L-Lysine monohydrate 0.24 g was added to the mixture, and the resulting mixture was held at room temperature for 30 minutes with continuous mixing to form a slurry solution.

24.89 g of calcium hydroxide was added to the slurry solution and the mixture was heated to 85–90 degrees C. The temperature was maintained at 85–90 degrees C for 2 hours with continuous mixing. The solution of the partial salt was discharged into trays (while maintaining batch temperature and mixing speed), and the solution was heated in an 85 degree C oven until dry.

The salt was milled and used to make a denture adhesive cream formula. This salt is 0.3 Lysine-70 Ca GANTREZ Salt. Using different amounts of lysine and metal oxides, different percentages of substitution of Lysine-GANTREZ Salts were prepared and used to make denture adhesive creams by combining 30% of the salt (by weight) with 24% by weight carboxymethyl cellulose, 18% by weight mineral oil and 28% by weight petrolatum. A comparative example of a denture adhesive cream was made without lysine.

The shear strength of the denture adhesive creams were measured and the results are shown in Table 2. The shear strength was measured with an Instron Model 1122. Denture adhesive creams made with lysine cross-linked GANTREZ copolymer partial Ca salts show improved performance.

TABLE 2

Shear Strength

| Material Tested | Shear Strength (g/in$^2$) |
|---|---|
| 0.0% lysine; 65% calcium | 590 |
| 0.3% lysine; 65% calcium | 787 |
| 0.5% lysine; 65% calcium | 689 |
| 0.7% lysine; 65% calcium | 708 |
| 0.0% lysine; 70% calcium | 673 |
| 0.3% lysine; 70% calcium | 877 |
| 0.5% lysine; 70% calcium | 696 |
| 0.7% lysine; 70% calcium | 795 |

Examples 18–19

A 0.5 percent substitution lysine, 40 percent substitution Zinc, 20 percent substitution Magnesium, and 10 percent substitution Sodium methylvinyl ether maleic acid copolymer salt was prepared by adding 75.93 9 of GANTREZ AN 169 to 1,000 ml. of vigorously mixed deionized water. Then 0.40 9 L-Lysine monohydrate was added to the mixture, and the resulting mixture was held at room temperature for 30 minutes with continuous mixing.

A solution of 250 ml of deionized water containing 15.85 g zinc oxide, 3.93 g magnesium oxide and 3.90 g sodium hydroxide was added gradually to the lysine GANTREZ AN slurry and the mixture was heated to 85–90 degrees C and held at that temperature for 2 hours with continuous mixing. The solution of the partial salt was discharged into trays (while maintaining batch temperature and mixing speed), and the salt was heated at 85 degrees C until dry. The dry salt was milled and used to make a denture adhesive cream formula.

A small consumer test showed that the denture adhesive cream made with the above salt was preferred over a comparative example, a denture adhesive made with a similar salt without lysine.

The purpose of the above description is to illustrate some embodiments of the present invention without implying a limitation. It will be apparent to those skilled in the art that various modifications and variations may be made in the apparatus or procedure of the invention without departing from the scope or spirit of the invention.

What is claimed is:

1. A denture adhesive comprising a safe and effective amount of a cross-linked partial copolymer salt, wherein:
    a) a staring material being a copolymer of an anhydride form which is at least partially cross-linked by amide linkages through a cross-linking agent selected from the group consisting of lysine, histidine, arginine, non-toxic derivatives or family members of lysine, histidine or arginine and mixtures thereof, and subsequently converted to a partial salt/partial acid; and
    b) the cross-linked copolymer partial salt/partial acid comprises a cationic salt function selected from the group consisting of calcium, magnesium, strontium, sodium, potassium, zirconium, zinc, iron, tin and mixtures thereof.

2. The denture adhesive of claim 1, wherein said adhesive is formulated as a liquid, powder, cream, paste, gel or liner.

3. The denture adhesive of claim 2, wherein said copolymer comprises an alkyl vinyl ether and a copolymerizable unsaturated alkyl anhydride.

4. The denture adhesive of claim 2, wherein said polymer is selected from the group consisting of: a) a copolymer comprising an alkylvinyl ether and a vinyl ether copolymerizable carboxylic acid anhydride; and b) a copolymer comprising an alkylvinyl ether and maleic anhydride.

5. The denture adhesive of claim 4, wherein said alkylvinyl ether is methylvinyl ether.

6. The denture adhesive of claim 1, wherein the percent substitution of amino groups of said lysine or its nontoxic derivatives or family members in the polymer is less than about 20% and more than about 0.01%.

7. The denture adhesive of claim 6, wherein the percent substitution of amino groups of said lysine or its nontoxic derivatives or family members in said cross-linking agent in the copolymer is more than about 0.1% and less than about 10%.

8. The denture adhesive of claim 7, wherein the percent substitution of amino groups of said lysine or its nontoxic derivatives or family members in said agent in the copolymer is more than about 0.05% and less than about 1%.

9. A method of making a denture adhesive material comprising the steps of:
    (a) forming a partially cross-linked by amide linkages copolymer from a copolymer of an anhydride form by reacting said copolymer of an anhydride form with a cross-linking agent selected from the group consisting of lysine, histidine, arginine, nontoxic derivatives or family members of lysine, histidine or arginine and mixtures thereof;
    (b) hydrolyzing the remaining anhydride groups in said partially cross-linked copolymer to form a carboxylic acid; and
    (c) at least partially neutralizing said carboxylic acid groups to form a partial salt of a cross-linked copolymer.

10. The method of claim 9, where said steps of forming, at least partially hydrolyzing and at least partially neutralizing are carried out in a single reaction vessel.

11. The method of claim 9, further comprising the step of combining said partial salt of a cross-linked copolymer with a excipient and a carrier to form a denture adhesive material.

12. The method of claim 10, further comprising the step of combining said partial salt of a cross-linked copolymer with a carrier to form a denture adhesive material.

13. A copolymer salt which is at least partially cross-linked by amide lineages through a cross-linking agent selected from the group consisting of lysine, histidine, arginine, nontoxic derivative or family members of lysine, histidine or arginine or mixtures thereof, wherein said copolymer is a copolymer of a polymerizable ether and a polymerizable anhydride.

14. The denture adhesive composition of claim 1, further comprising at least one member selected from the group consisting of water soluble polymers, fillers, lubricants, flavors, coloring agents, and preservatives.

15. A partial salt/partial acid with a starting material of a copolymer of an anhydride form which is at least partially cross-linked by amide linkages through a cross-linking agent selected from the group consisting of lysine, histidine, arginine, derivative or family members of lysine, histidine or arginine or mixtures thereof, wherein said copolymer is a copolymer of a polymerizable ether and a polymerizable acid or anhydride and said partial salt/partial acid further comprises a cationic salt function selected from the group consisting of calcium, magnesium, strontium, sodium, potassium, zirconium, zinc, iron, tin and mixtures thereof.

* * * * *